United States Patent
Intoccia, Jr. et al.

(10) Patent No.: US 9,808,330 B2
(45) Date of Patent: Nov. 7, 2017

(54) BODILY IMPLANT WITH TENSION INDICATOR

(75) Inventors: Alfred P. Intoccia, Jr., Nashua, NH (US); Timothy P. Harrah, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 540 days.

(21) Appl. No.: 13/598,128

(22) Filed: Aug. 29, 2012

(65) Prior Publication Data

US 2013/0060078 A1   Mar. 7, 2013

Related U.S. Application Data

(60) Provisional application No. 61/530,514, filed on Sep. 2, 2011.

(51) Int. Cl.
*A61F 2/02* (2006.01)
*A61F 2/00* (2006.01)

(52) U.S. Cl.
CPC ......... *A61F 2/0045* (2013.01); *A61F 2/0077* (2013.01); *A61F 2002/0068* (2013.01); *A61F 2250/0018* (2013.01); *A61F 2250/0048* (2013.01); *A61F 2250/0097* (2013.01)

(58) Field of Classification Search
CPC ...... A61F 2250/0097; A61F 2250/0024; A61F 2002/0068
See application file for complete search history.

(56) References Cited

U.S. PATENT DOCUMENTS

| | | | |
|---|---|---|---|
| 7,766,926 B2* | 8/2010 | Bosley, Jr. | A61B 17/06109 600/30 |
| 2003/0216814 A1* | 11/2003 | Siegel | A61F 2/0045 623/23.66 |
| 2004/0260315 A1* | 12/2004 | Dell | A61F 2/0063 606/151 |
| 2006/0089525 A1 | 4/2006 | Mamo et al. | |
| 2007/0282160 A1* | 12/2007 | Sheu et al. | 600/30 |
| 2008/0269552 A1* | 10/2008 | Montpetit et al. | 600/37 |
| 2009/0076318 A1* | 3/2009 | Li | A61F 2/0045 600/30 |
| 2009/0192346 A1* | 7/2009 | Rosenblatt | 600/30 |
| 2010/0261950 A1* | 10/2010 | Lund et al. | 600/30 |
| 2011/0105831 A1* | 5/2011 | Staskin et al. | 600/30 |
| 2011/0112357 A1* | 5/2011 | Chapman et al. | 600/37 |
| 2011/0144417 A1* | 6/2011 | Jagger et al. | 600/30 |
| 2012/0184973 A1* | 7/2012 | Mathisen | A61F 2/0063 606/151 |
| 2013/0018219 A1* | 1/2013 | Khamis et al. | 600/30 |

OTHER PUBLICATIONS

May Clinic Staff, "Urinary Incontinence Surgery: When Other Treatments Aren't Enough", Mayo Clinic, Mar. 26, 2011, 7 pages.

* cited by examiner

*Primary Examiner* — Catherine B Kuhlman
*Assistant Examiner* — Shannon McBride
(74) *Attorney, Agent, or Firm* — Brake Hughes Bellermann LLP

(57) ABSTRACT

A bodily implant is provided to support body tissues of a patient. The bodily implant includes a strip having a first portion and a second portion. The strip is configured to be stretched in a manner such that the second portion is stretched from a first length to a second length. The second portion of the strip is configured to maintain the second length. The strip is further configured to be disposed proximate to the patient's body tissues.

20 Claims, 10 Drawing Sheets

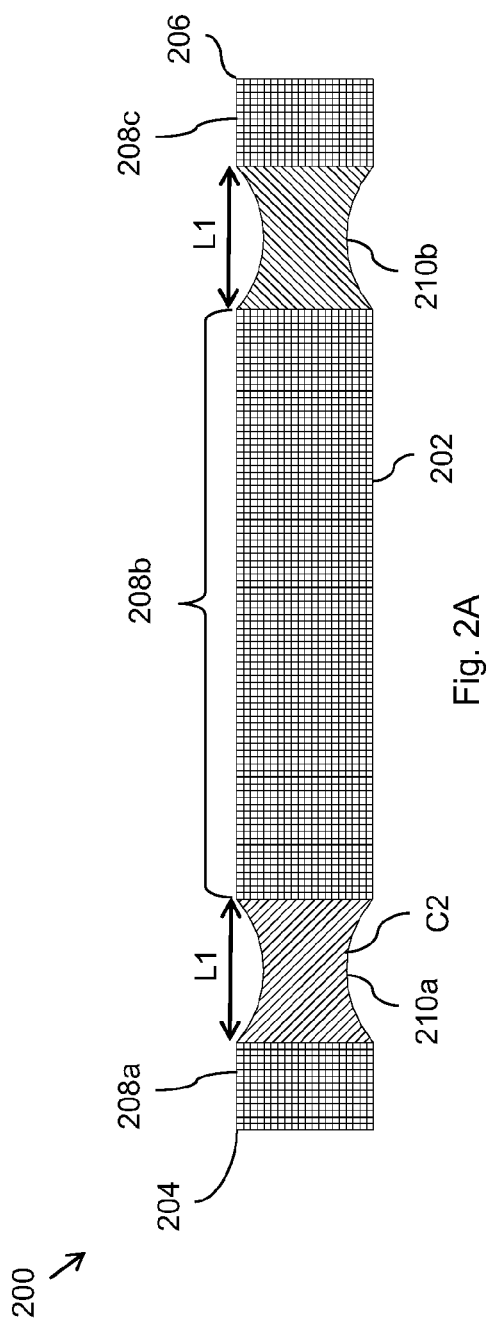
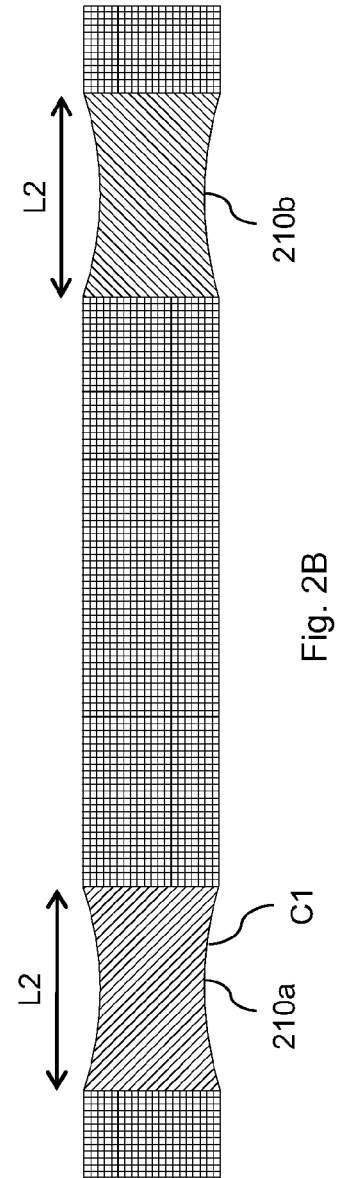
Fig. 2A
Fig. 2B

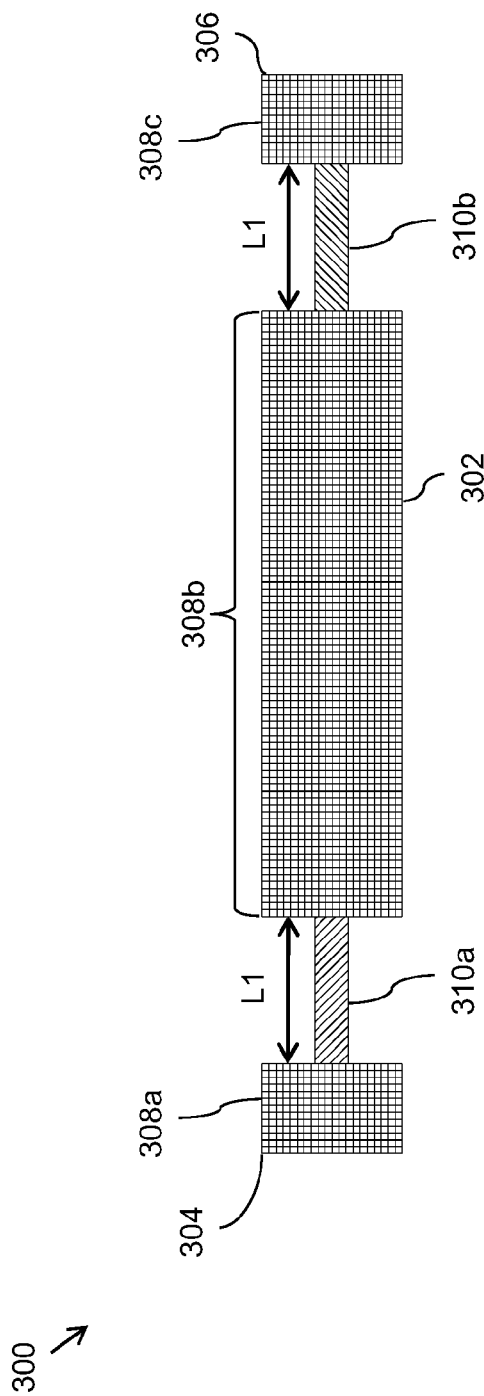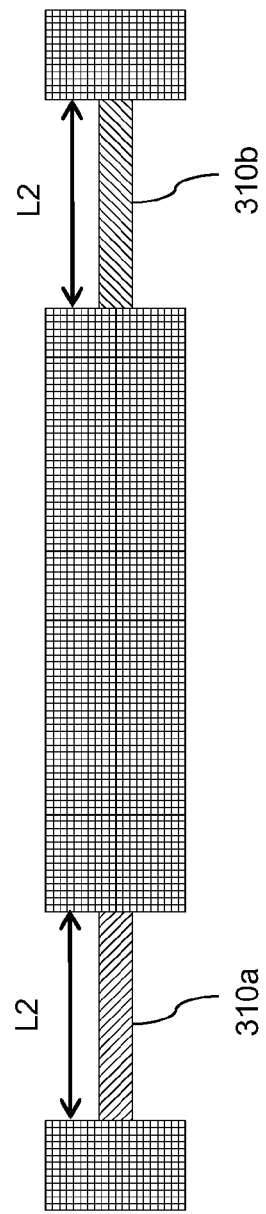

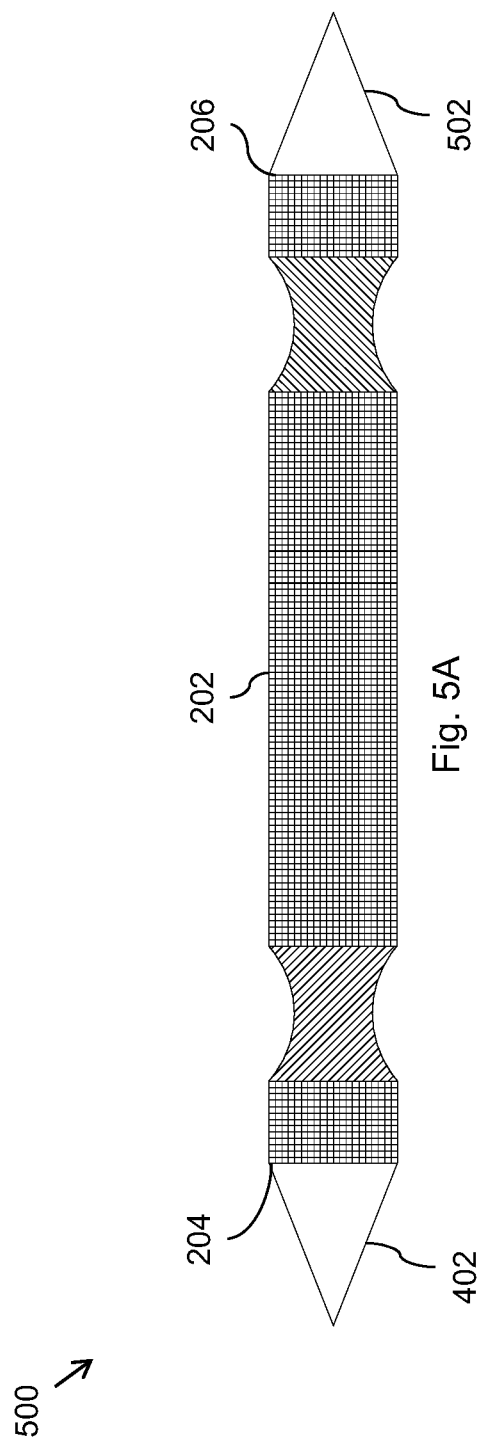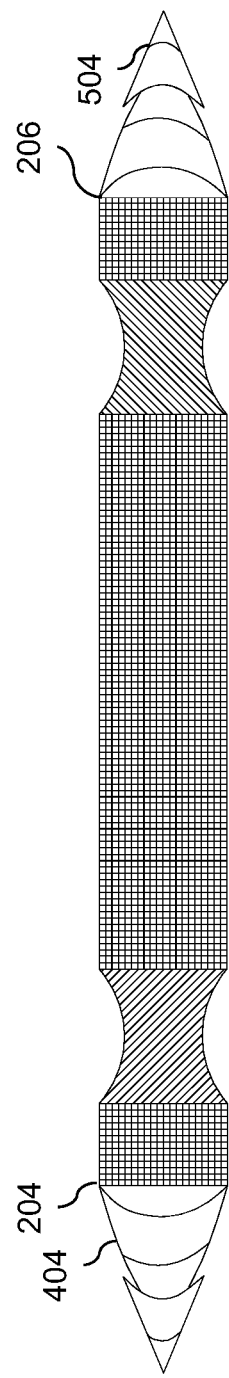

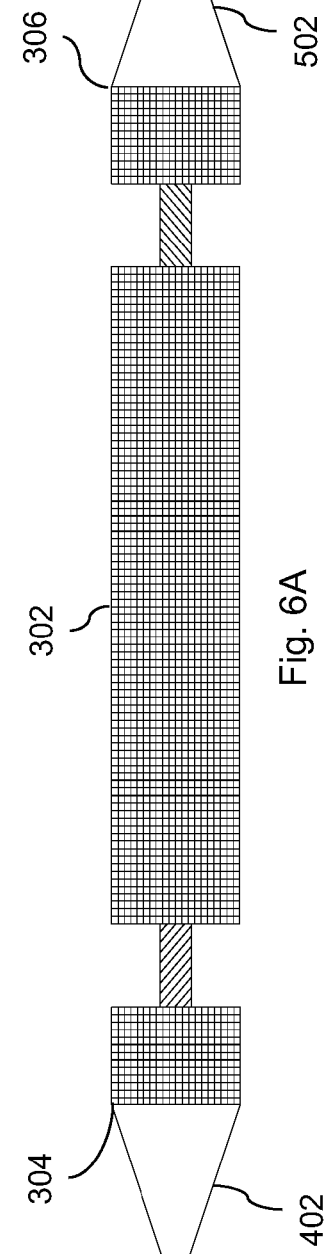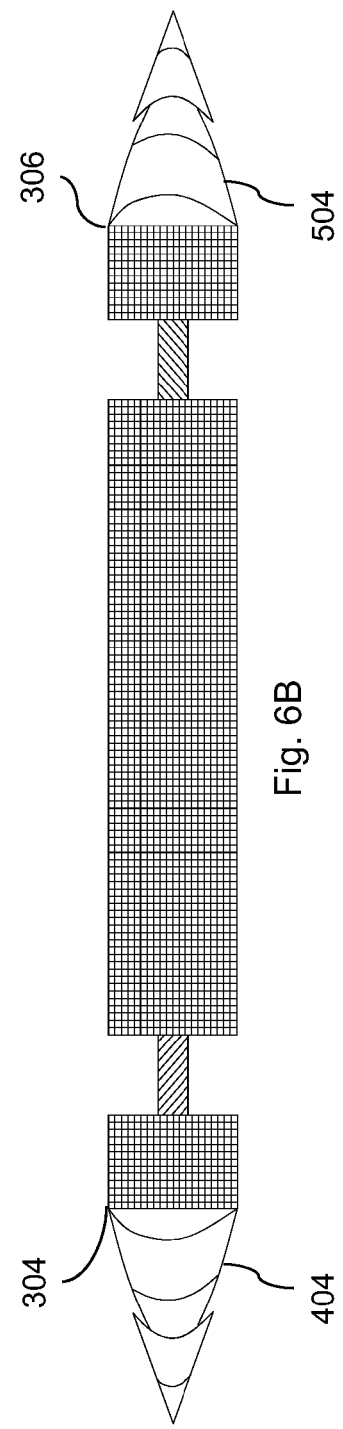

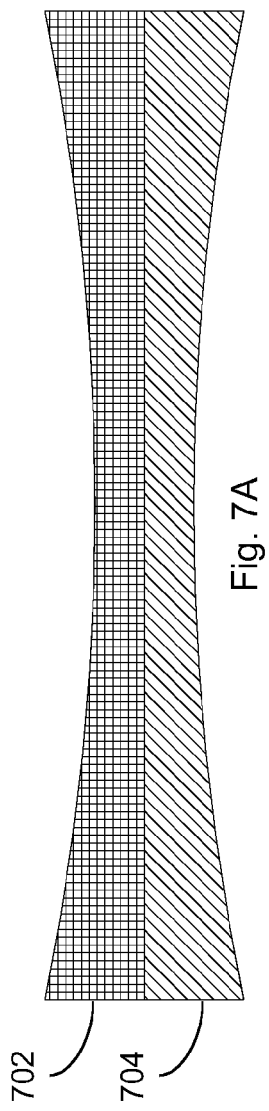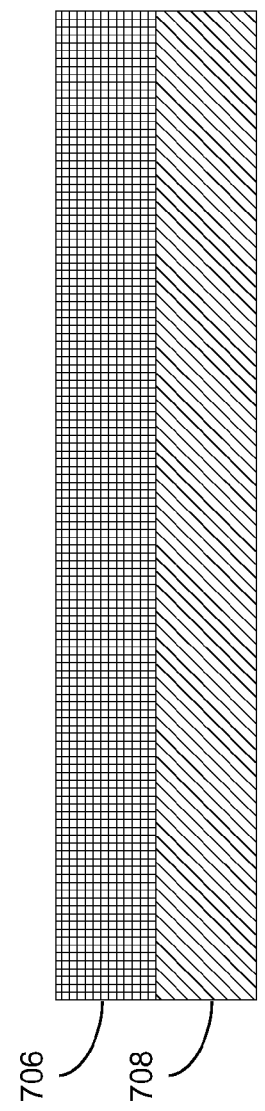

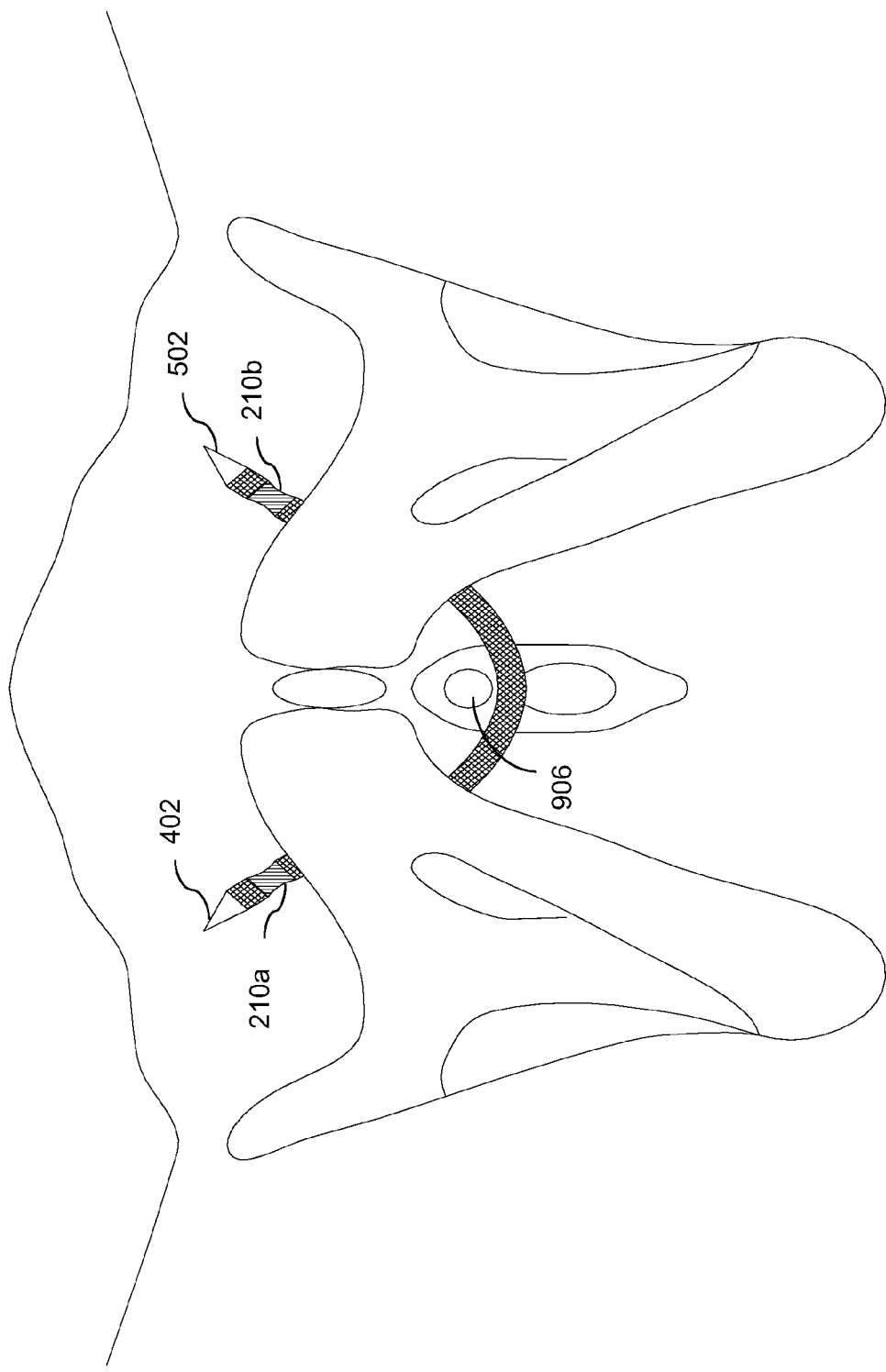

BODILY IMPLANT WITH TENSION INDICATOR

CROSS-REFERENCE TO RELATED APPLICATION

This application is a Nonprovisional of, and claims priority to, U.S. Patent Application No. 61/530,514, filed Sep. 2, 2011, entitled "BODILY IMPLANT WITH TENSION INDICATOR", which is incorporated by reference herein in its entirety.

BACKGROUND

Field

The invention generally relates to medical devices and procedures, and more particularly bodily implants and their implantation into a body of a patient to support body tissues.

Description of the Related Art

Urinary Incontinence (UI) is loss of bladder control, which results in involuntary leakage of urine. Incontinence may be caused by many different medical problems in muscles and nerves that help to hold or release urine. The four basic types of UI are stress incontinence, urge incontinence, mixed incontinence, and overflow incontinence. Stress Urinary Incontinence (SUI) is a condition in which a patient leaks urine due to a sudden increase in the abdominal pressure. This increase in abdominal pressure can result from daily activities such as laughing, sneezing, walking, and the like.

Another type of incontinence that involves involuntary passage of feces through an anal canal is fecal incontinence. This type of disorder may be caused due to weakness or damage of internal and external anal sphincter muscles or levator ani muscles surrounding the anal canal in a human body.

A variety of surgical and non-surgical techniques are adopted to treat disorders and damages associated with UI and fecal incontinence. One such surgical treatment includes a sling procedure in which bodily implants such as slings are disposed into a patient's body, e.g., around a bladder neck to treat UI and around the anal canal to treat fecal incontinence.

The sling procedure may be performed using strips of natural materials, such as body tissue, or synthetic material or mesh (e.g., polypropylene mesh). In some embodiments, slings can have high rates of effectiveness and low risks of complications. In the recent years, the synthetic sling materials have gained popularity along with the procedure of placing the sling in the area of the mid-urethra to treat UI.

In some cases, the sling procedure is performed under either a general or spinal anesthetic. The UI sling procedure may be performed using either a pubovaginal technique or a transvaginal technique. In the pubovaginal technique, an incision is made above a pubic bone and another incision is made in a vaginal wall, through which the sling is grasped and adjusted around the bladder neck. The sling is then secured by two sutures that are loosely tied to each other above the pubic bone incision, thus providing a hammock like support to the bladder neck. However, in the transvaginal technique, a small incision is made only in the vaginal wall of the patient. The sling is then inserted into the vagina through this incision to support the bladder, the bladder neck, a urethra, and a urethral sphincter of the patient. Irrespective of the sling technique used, the placement of the sling inside the body of the patient helps to restore the normal urinary function of the patient.

During the sling procedure, the amount of tension may be difficult to determine and may involve the use of tests during surgery to determine the compression effect of the sling on the body tissues (such as in urethra in case of the UI treatment) that are supported by the sling. Some manual tests may be performed, or a more sophisticated urodynamic test like cystourethrography, may determine tension. It may be important for a surgeon to test or determine tension during surgery because of the high rate of urine retention (inability to void) associated with this procedure and to avoid miscalculation of the required tension.

In an existing solution to determine the tension, the surgeon places a tubular member such as a hemostat between the sling and the body tissues such as urethra. The tubular member facilitates measurement of an extra amount of material between the sling and the body tissue that is supported by the sling. The extent of the slack between the sling and the body tissue is determined based on the size of the tubular member being used.

In accordance with the foregoing, there is a need for devices and methods for providing an improved bodily implant that ensures an appropriate amount of slack between the sling and the body tissues (that are being supported by the sling) so that the sling is neither left too loose nor tight within the body of the patient.

SUMMARY

A bodily implant for the treatment of urinary and fecal incontinence is provided. The bodily implant includes a strip having a first portion and a second portion. The strip is configured to be stretched in a manner such that the second portion is stretched from a first length to a second length. The second portion of the strip is configured to maintain the second length. The strip is further configured to be disposed proximate to the patient's body tissues to support the patient's body tissues.

Further, a support system including a strip, a first anchor, and a second anchor is provided. The strip has a first portion and a second portion. The strip is configured to be stretched in a manner such that the second portion is stretched from a first length to a second length. The second portion of the strip is configured to maintain the second length. The strip is further configured to be disposed proximate to the patient's body tissues to support the patient's body tissues. The first and second anchors are disposed at opposite ends of the strip. The first and second anchors are configured to help retain the strip in place within the patient.

BRIEF DESCRIPTION OF THE FIGURES

The invention and the following detailed description of certain embodiments thereof may be understood with reference to the following figures:

FIGS. 2A and 2B illustrate perspective views of a bodily implant configured to be delivered into the body of the patient, in accordance with an embodiment of the invention;

FIGS. 3A and 3B illustrate perspective views of a bodily implant configured to be delivered into the body of the patient, in accordance with another embodiment of the invention;

FIGS. 5A and 5B illustrate a perspective view of a support system including anchors coupled to the bodily implant of FIG. 2A, in accordance with an embodiment of the invention;

FIGS. 6A and 6B illustrate a perspective view of a support system including anchors coupled to the bodily implant of FIG. 3A, in accordance with another embodiment of the invention;

FIGS. 7A and 7B illustrate a layered structure of second portions of the bodily implants of FIGS. 2A and 3A, in accordance with an embodiment of the invention;

FIG. 10 is an illustrative method of positioning the support system of FIG. 5A within the patient's body, in accordance with an embodiment of the invention.

DETAILED DESCRIPTION

Figure 1:
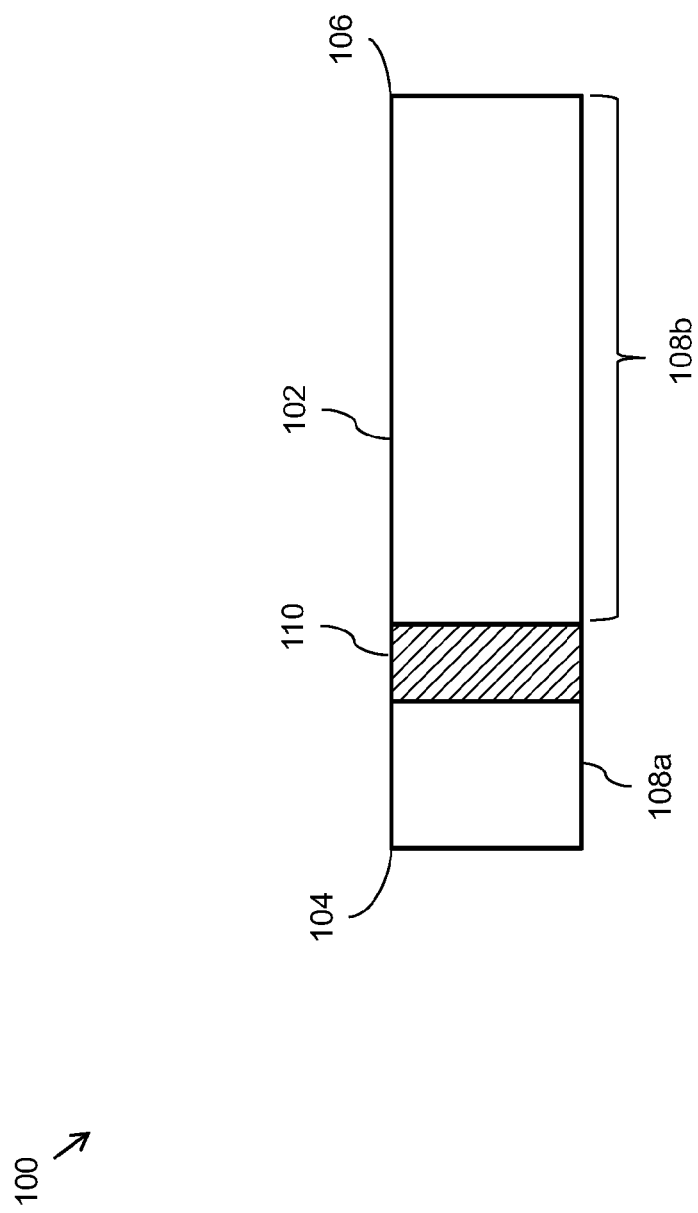
FIG. 1 is a schematic diagram of a bodily implant configured to be delivered into a body of a patient, in accordance with an embodiment of the invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having," as used herein, are defined as comprising (i.e., open transition). The term "coupled" or "operatively coupled," as used herein, is defined as connected, although not necessarily directly and mechanically.

The terms proximal and distal described in relation to various devices, apparatuses, and components (as discussed in the subsequent text of the present invention) are disclosed with a point of reference. The point of reference, as used in this description, is a perspective of an operator. The operator may be a surgeon, a physician, a nurse, a doctor, a technician, or the like, who may perform the procedure of delivery and placement of a bodily implant into a body of a patient as described in the present invention. The patient may be a human female, a human male, or any other mammal. The term proximal refers to an area that is closest to the operator. The term distal refers to an area that is farthest from the operator.

The present invention relates to devices and methods for implantation of an improved bodily implant into a body of a patient. In one embodiment, the bodily implant may be used for the treatment of urinary incontinence. In this case, the bodily implant is designed to provide support to body tissues that form a body organ such as a urethra and a bladder neck of the patient. The placement of the bodily implant inside the body of the patient restores the normal urinary function of the patient. In another embodiment, the bodily implant may be used for the treatment of fecal incontinence. In this case, the bodily implant is placed inside the body of the patient around an anal canal, or a rectum, or an anus of the patient to prevent the involuntary passage of feces. Irrespective of the type of incontinence to be treated, the bodily implant is inserted into the body of the patient and stretched in a manner such that the stretched bodily implant is disposed proximate to the body tissues to be supported (hereinafter interchangeably referred to as supported body tissues). In some embodiments, the bodily implant is stretched to a length such that an appropriate slack is achieved between the bodily implant and the supported body tissues. In other words, the bodily implant, which when placed inside the body of the patient, ensures that the contact between the bodily implant and the body tissues is neither left too loose nor tight.

FIG. 1 is a schematic diagram of a bodily implant 100 configured to be delivered into a body of a patient, in accordance with an embodiment of the invention. The bodily implant 100 may be a sling system that is utilized in the treatment of urinary or fecal incontinence. The bodily implant 100 defines a strip 102 that extends along a length between a first end 104 and a second end 106 that is opposite to the first end 104.

The strip 102 is configured to be placed within the patient's body. In some embodiments, the strip 102 may possess elastic property and thus, may be stretched to a certain length. In an embodiment, the strip 102 is formed of a material that allows tissue in-growth after implantation within the patient's body. As illustrated in FIG. 1, the strip 102 defines a first portion 108a, a first portion 108b, and a second portion 110 (illustrated by the shaded portion in FIG. 1) that is disposed between the first portions 108a and 108b. In some embodiments, the first portions 108a and 108b may be constructed from a material with different properties than that of the second portion 110. In an embodiment, the first portions 108a and 108b are made of a material such that they are configured to stretch at a first tensile force. The point at which the material begins to stretch is hereinafter referred to as the stretching point. Hence the stretching point of the first portions 108a or 108b is the point at which the first portions 108a or 108b begins to stretch when the first tensile force is applied. In various embodiments, the first tensile force is greater than the force at which the stretching point of the first portions 108a or 108b is achieved. The types of material used to fabricate and manufacture existing bodily implants are described below. The second portion 110 is made of a material such that the second portion 110 is configured to stretch at a second tensile force. Hence the stretching point of the second portion 110 is the point at which the second portion 110 begins to stretch when the second tensile force is applied. In various embodiments, the second tensile force is greater than the force at which the stretching point of the second portion 110 is achieved. The material used for the second portion 110 may include a polymer such as, but not limited to, polyolefin or silicone rubber. In various embodiments, the second tensile force is less than the first tensile force. In such a case, the operator may stretch the strip 102 with the second tensile force such that only the second portion 110 reaches or crosses its stretching point without stretching the rest of the strip 102 (i.e., the first portions 108a and 108b). Alternatively, in another embodiment, the first portions 108a and 108b may also stretch to a certain length when the second tensile force is applied on the strip 102.

The second tensile force applied on the strip 102 results in the second portion 110 stretching from an existing length (hereinafter interchangeably referred to as a first length) to another length (hereinafter interchangeably referred to as a second length). In some embodiments, the second length refers to the stretched length of the second portion 110 at which an appropriate slack is achieved between the bodily implant 100 and the patient's body tissues. In an embodiment, the second portion 110 of the strip 102 is configured to provide an indication of the stretching of the second portion 110, i.e., when the second portion 110 is being stretched to the desired length (second length in this case). The configuration and process of providing this indication is explained later in conjunction with FIGS. 7A and 7B. In embodiments, the second portion 110 of the strip 102 is configured to maintain this second length. This maintained length facilitates the operator to dispose the strip 102 at an appropriate location proximate to the body tissues to be supported. In an embodiment, the strip 102 is designed to provide support to body tissues that form a body organ such as a urethra and a bladder neck, i.e., in the case of treatment of urinary incontinence.

In accordance with various embodiments for implantation of the bodily implant 100 within the patient's body, an operator may deliver the strip 102 to a periurethral tissue of the patient. According to various embodiments, the invention makes it easier for the operator to accurately place the bodily implant 100 at a desired anatomical location.

The length and width of the strip 102 may vary based on the intended use of the bodily implant 100. The strip 102 can be of various sizes, shapes, and configurations depending on the intended use and locations of placement of the bodily implant 100. The strip 102 can be shaped and sized according to the body tissues to be supported. In some embodiments, the strip 102 may include one or more support members disposed on the first end 104 and the second end 106 of the strip 102. The support members may be of different shapes such as rectangular, oval, circular, elliptical, and the like.

Various types of woven tapes, fabrics, or meshes may be utilized in fabricating and manufacturing the strip 102, in accordance with various embodiments. The strip 102 may utilize a variety of mesh materials and may be designed in different forms. An example of a mesh utilized in the strip is Polyform® Synthetic Mesh developed by the Boston Scientific Corporation. The Polyform® Synthetic Mesh is made from uncoated monofilament macro-porous polypropylene. The strip 102 may also be made from a biological material or a cadaveric tissue. Additionally, the strip 102 may be stretchable and flexible to adapt movements in accordance with the anatomy of the human body. Furthermore, softness, lightness, conformity, and strength are certain other attributes required in the strip 102 for efficient tissue repair and implantation. In an embodiment, the strip 102 can have a coating. For example, the strip 102 can be coated with an antimicrobial agent and/or an antifungal agent.

The size and shape of the strip 102, the first portions 108a and 108b, and the second portion 110 as illustrated in FIG. 1 are merely exemplary, and various other shapes and sizes are possible without limiting the spirit and scope of the present invention. In some embodiments, the strip 102 may include a plurality of second portions similar to the second portion 110. In an exemplary embodiment, the strip 102 may include a second portion with a configuration similar to that of the second portion 110. This second portion (and/or the second portion 110) may be disposed anywhere along the length of the strip 102. In an exemplary embodiment, this second portion (and/or the second portion 110) may be disposed proximate to the second end 106 of the strip 102.

FIGS. 2A and 2B illustrate perspective views of a bodily implant 200 configured to be delivered into the body of the patient, in accordance with an embodiment of the invention.

The bodily implant 200 may be a sling system that is utilized in the treatment of urinary or fecal incontinence. The bodily implant 200 includes a strip 202 that extends along a length between a first end 204 and a second end 206 that is opposite to the first end 204. As shown in FIGS. 2A and 2B, the strip 202 has a rectangular shape.

The strip 202 is configured to be placed within the patient's body. In some embodiments, the strip 202 may possess elastic property and thus, may be stretched to a certain length. In an embodiment, the strip 202 is formed of a material that allows tissue in-growth after implantation within the patient's body. The strip 202 defines first portions 208a, 208b, and 208c (illustrated by crossed lines in FIGS. 2A and 2B) and second portions 210a and 210b (illustrated by hatched lines in FIGS. 2A and 2B). The second portion 210a is disposed between the first portions 208a and 208b, whereas the second portion 210b is disposed between the first portions 208b and 208c. As illustrated in FIGS. 2A and 2B, the first portions 208a, 208b, and 208c have a linear shape, whereas the second portions 210a and 210b have a curved shape. As illustrated in FIG. 2A, the strip 202 is in a non-stretched configuration in which the length of the second portion 210a or the second portion 210b is defined as L1. The second portion 210a is disposed proximate to the first end 204 of the strip 202, whereas the second portion 210b is disposed proximate to the second end 206 of the strip 202. In an embodiment, one of the second portions 210a or 210b may be optional. In some embodiments, the first portions 208a, 208b, and 208c may be constructed from a material with different properties than that of the second portions 210a and 210b. In some embodiments, the first portions 208a, 208b, and 208c are made of a material such that they may stretch at a first tensile force. The second portions 210a and 210b are made of a material such that the second portions 210a and 210b are configured to stretch at a second tensile force that is less than the first tensile force. The material used for the second portions 210a and 210b may include a polymer such as, but not limited to, polyolefin or silicone rubber.

As illustrated in FIG. 2B, the strip 202 is in a stretched configuration. In some embodiments, the strip 202 is configured to be stretched when the second tensile force is applied on the strip 202 such that the second portions 210a and 210b are stretched from the existing length L1 to a length L2. For example, the second portion 210a or 210b may be stretched from 2 centimeters (i.e., in the non-stretched configuration) to 10 centimeters (i.e., in the stretched configuration) once the second tensile force is applied on the strip 202. The second tensile force applied on the strip 202 results in the second portions 210a and 210b to reach or cross the stretching point without stretching the rest of the strip 202 (i.e., the first portions 208a, 208b, and 208c). In some embodiments, the length L2 refers to the stretched length at which an appropriate slack is achieved between the bodily implant 200 and the patient's body tissues. As shown in FIGS. 2A and 2B, the curvature C1 and thickness of the second portions 210a and 210b after being stretched to the length L2 (as illustrated in FIG. 2B) is less than the curvature C2 and thickness of the second portions 210a and 210b before being stretched (as illustrated in FIG. 2A).

In an embodiment, the second portions 210a and 210b are configured to provide an indication of the stretching of the second portions 210a and 210b, i.e., when the second portions 210a and 210b are stretched to the desired length L2. In various embodiments, the indication may be a visual such as, but not limited to, change in the color of the second portions 210a and/or 210b or display of a letter, a number, or a line. For example, in some embodiments, the indication may be a color change that is accomplished by a polymer or mechanosensitive molecules that facilitate a color change in the material (for example, when the material is placed under a stress such as a stretching force). In some embodiments, the second portion 210a or 210b of the strip 202 is configured to maintain the length L2. This maintained length facilitates the operator to dispose the strip 202 at an appropriate location proximate to the body tissues to be supported. In an embodiment, the strip 202 is designed to provide support to body tissues that form a body organ such as a urethra and a bladder neck, i.e., in the case of treatment of urinary incontinence.

In some embodiments, the strip 202 is formed of a knitted material. In some embodiments, the second portions 210a and 210b may be formed of the knitted material and have a different knit pattern than the remainder of the strip 202. The different knit pattern of the second portions 210a and 210b may allow the second portions 210a and 210b to deform or extend to the desired length or tension while the reminder of the strip 202 remains unmodified.

The length and width of the strip 202 may vary based on the intended use of the bodily implant 200. The strip 202 can be of various sizes, shapes, and configurations depending on the intended use and locations of placement of the bodily implant 200 within the body of the patient. The strip 202 can be shaped and sized according to the body tissues to be supported. In some embodiments, the strip 202 may include one or more support members disposed on the first end 204 and the second end 206 of the strip 202. The support members may be of different shapes such as rectangular, oval, circular, elliptical, and the like.

The size and shape of the strip 202, the first portions 208a, 208b, and 208c, and the second portions 210a and 210b as illustrated in FIGS. 2A and 2B are merely exemplary, and various other shapes and sizes are possible without limiting the spirit and scope of the present invention. For example, the strip 202 may have an oval shape to provide better distribution of tension to the body tissues, thereby minimizing tissue damage and erosion.

FIGS. 3A and 3B illustrate perspective views of a bodily implant 300 configured to be delivered into the body of the patient, in accordance with another embodiment of the invention. The bodily implant 300 may be a sling system that includes a strip 302 that extends along a length between a first end 304 and a second end 306 that is opposite to the first end 304. The strip 302 defines first portions 308a, 308b, and 308c (illustrated by crossed lines in FIGS. 3A and 3B) and second portions 310a and 310b (illustrated by hatched lines in FIGS. 3A and 3B). The second portion 310a is disposed between the first portions 308a and 308b, whereas the second portion 310b is disposed between the first portions 308b and 308c. The functionalities and configurations of the bodily implant 300 may be similar to that of the bodily implant 200 as described above in conjunction with FIGS. 2A and 2B, except that the shape of the second portions 310a and 310b differs from that of the second portions 210a and 210b. As illustrated in FIGS. 3A and 3B, the first portions 308a, 308b, and 308c and the second portions 310a and 310b have a linear shape. Also, the width of the second portions 310a and 310b is less than that of the first portions 308a, 308b, and 308c. As illustrated in FIG. 3A, the strip 302 is in a non-stretched configuration in which the length of the second portion 310a or the second portion 310b is defined as L1. As illustrated in FIG. 3B, the strip 302 is in a stretched configuration in which the strip 302 is configured to be stretched when the appropriate tensile force is applied on the strip 302 such that the second portions 310a and 310b are stretched from the existing length L1 to a length L2.

The length and width of the strip 302 may vary based on the intended use of the bodily implant 300. The strip 302 can be of various sizes, shapes, and configurations depending on the intended use and locations of placement of the bodily implant 300 within the body of the patient. The strip 302 can be shaped and sized according to the body tissues to be supported. In some embodiments, the strip 302 may include one or more support members that may be disposed on the first end 304 and the second end 306 of the strip 302. The support members may be of different shapes such as rectangular, oval, circular, elliptical, and the like.

Figure 4B:
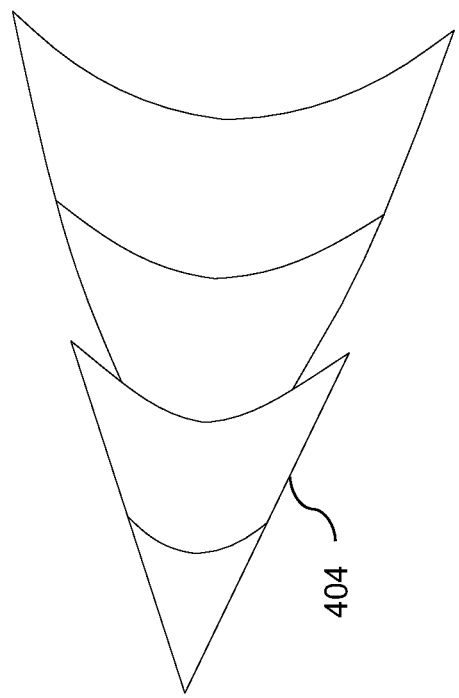
FIGS. 4A and 4B illustrate perspective views of support members, in accordance with an embodiment of the invention.
Figure 4A:
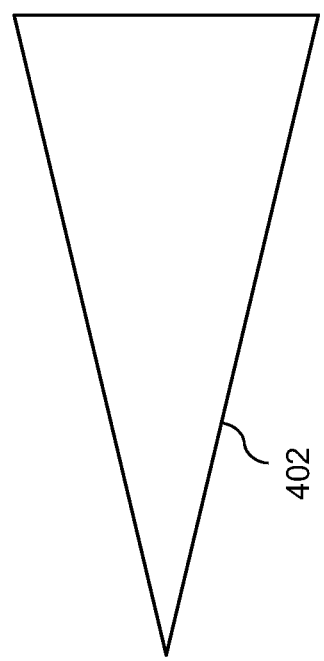

FIGS. 4A and 4B illustrate perspective views of support members such as anchors 402 and 404, in accordance with an embodiment of the invention. The anchor 402 or 404 may be configured to be attached to an end of a bodily implant (such as the bodily implants 100, 200, or 300) so as to help retain that bodily implant in place within the body of the patient. In accordance with various embodiments, the position of the anchor 402 or 404 inside the patient's body is fixed once the anchor 402 or 404 is placed inside the patient's body. In order to achieve the appropriate slack between the bodily implant and the patient's body tissues, the operator may then pull the bodily implant without causing any change in the position of the anchor 402 or 404. The anchor 402 in FIG. 4A is a triangular shaped support member, whereas the anchor 404 in FIG. 4B is semi-triangular in shape with the base of the anchor 404 being curved.

In an embodiment, the base of the anchors 402 and 404 may optionally have another portion that may be shaped and sized to be coupled to the bodily implant (such as the bodily implants 100, 200, or 300). In various embodiments, the anchors 402 and 404 may be made of any suitable biocompatible material. In an exemplary embodiment, the anchors 402 and 404 may be made of a synthetic material such as nylon, polyethylene, polyester, polypropylene, fluoropolymers or a co-polymer. In another embodiment, a mammalian tissue material such as bovine, porcine, equine, human cadaveric or engineered tissue may be used. In yet another embodiment, the material of the anchors 402 and 404 may include a combination of synthetic and mammalian tissue materials. According to some embodiments, at least a portion of the anchors 402 and 404 is biodegradable and may also dissolve and/or be absorbed into the patient's body tissues.

The size and shape of the anchors 402 and 404 as illustrated in FIGS. 4A and 4B are merely exemplary, and various other shapes and sizes are possible without limiting the spirit and scope of the present invention.

FIGS. 5A and 5B illustrate a perspective view of a support system 500 including anchors coupled to the bodily implant 200 of FIG. 2A, in accordance with an embodiment of the invention. As illustrated in FIG. 5A, the anchor 402 is coupled to the first end 204 of the strip 202, whereas an anchor 502 similar to the anchor 402 is coupled to the opposite second end 206 of the strip 202. Likewise, as illustrated in FIG. 5B, the anchor 404 is coupled to the first end 204 of the strip 202, whereas an anchor 504 similar to the anchor 404 is coupled to the opposite second end 206 of the strip 202.

FIGS. 6A and 6B illustrate a perspective view of a support system 600 including anchors coupled to the bodily implant 300 of FIG. 3A, in accordance with another embodiment of the invention. As illustrated in FIG. 6A, the anchor 402 is coupled to the first end 304 of the strip 302, whereas the anchor 502 is coupled to the opposite second end 306 of the strip 302. Likewise, as illustrated in FIG. 6B, the anchor 404 is coupled to the first end 304 of the strip 302, whereas the anchor 504 is coupled to the opposite second end 306 of the strip 302.

Alternatively, in some embodiments, the coupling between the anchor and the bodily implant may be removable.

The support system 500 or 600 including anchors in combination with the bodily implant may be used to treat urinary or fecal incontinence. The anchors described in conjunction with FIGS. 5A, 5B, 6A, and 6B are used to position the opposite ends of the bodily implant at anatomical locations. The anchor (402, 404, 502, or 504) may have edges, tapers, barbs, or other protrusions to anchor at least a portion of the anchor in place within the patient's body.

Further, the second portion (210a or 210b or 310a or 310b) of the bodily implant (200 or 300) may include two or more layers. FIG. 7A illustrates a layered structure of the second portion (210a or 210b) of the bodily implant 200 of FIG. 2A, in accordance with an embodiment of the invention. For ease of reference, this embodiment is described using the second portion 210a since the structure and configuration of both the second portions 210a and 210b are same. The second portion 210a may include an upper layer 702 (illustrated by crossed lines in FIG. 7A) and a lower layer 704 (illustrated by hatched lines in FIG. 7A). In some embodiments, only the upper layer 702 may be configured to crack or develop micro-fractures when the strip 202 is stretched to the second length L2 (hereinafter interchangeably referred to as the desired length). The cracks or the micro-fractures may result in providing an opening or openings in the strip 202 such that the lower layer 704, which is immediately below the upper layer 702, is visible to the operator or physician.

In accordance with an embodiment, the lower layer 704 may be colored such as blue, red, or the like, which is easily visible to a human eye. In such a case, when the cracks are developed in the upper layer 702, the color of the lower layer 704 is made visible to the human eye. In another embodiment, the lower layer 704 may be structured such that when the upper layer 702 cracks, the lower layer 704 is made visible to the human eye. For example, the indication may be a visual such as, but not limited to, display of a letter, a number, or a line. In various embodiments, the visibility of the lower layer 704 acts as an indication to the operator or physician that the second portion 210a has been stretched to the desired length. The operator may then stop any further stretching of the strip 102 and hence, maintain this desired length to achieve the appropriate amount of slack between the bodily implant 200 and the supported body tissues.

Alternatively, in another embodiment, the second portion 210a may be configured to be stretched even further from the second length L2 to a third length L3 in order to achieve a looser contact between the bodily implant 200 and the supported body tissues. In this case, the bodily implant 200 may be readjusted with the patient's body such that the second portion 210a is stretched from the second length to a third length. In this case, more cracks are developed in the upper layer 702 such that the lower layer 704 is clearly visible. The second portion 210a may then maintain this third length L3. In this case, the operator ensures that the second portion 210a is stretched to a limited extent such that the lower layer 704 is stretched to a point less than a breaking point of the lower layer 704. The breaking point may refer to the point at which the material of the lower layer 704 breaks. In an exemplary embodiment, the operator may observe a lighter color of the lower layer 704 as an indication that the second portion 210a has been stretched to the second length L2. The operator may further stretch the second portion 210a to the third length L3 at which the operator may observe a consistent dark color of the lower layer 704. The bodily implant 200 may then maintain the third length L3 of the second portion 210a.

FIG. 7B illustrates a layered structure of the second portion (310a or 310b) of the bodily implant 300 of FIG. 3A, in accordance with another embodiment of the invention. The second portion 310a or 310b may include an upper layer 706 (illustrated by crossed lines in FIG. 7B) and a lower layer 708 (illustrated by hatched lines in FIG. 7B). The functionalities of the upper layer 706 and the lower layer 708 will be the same as the functionalities of the upper layer 702 and the lower layer 704, respectively.

The two layers of the second portion (210a, 210b, 310a, or 310b) as illustrated in FIGS. 7A and 7B are merely exemplary, and it may include any number of layers without limiting the spirit and scope of the present invention. In an exemplary embodiment, the second portion (210a, 210b, 310a or 310b) may include a middle layer that is disposed between the upper layer (702 or 706) and the lower layer (704 or 708). In some embodiments, the middle layer may be constructed from a material with same or different properties than that of the upper layer (702 or 706) or the lower layer (704 or 708).

Figure 8:
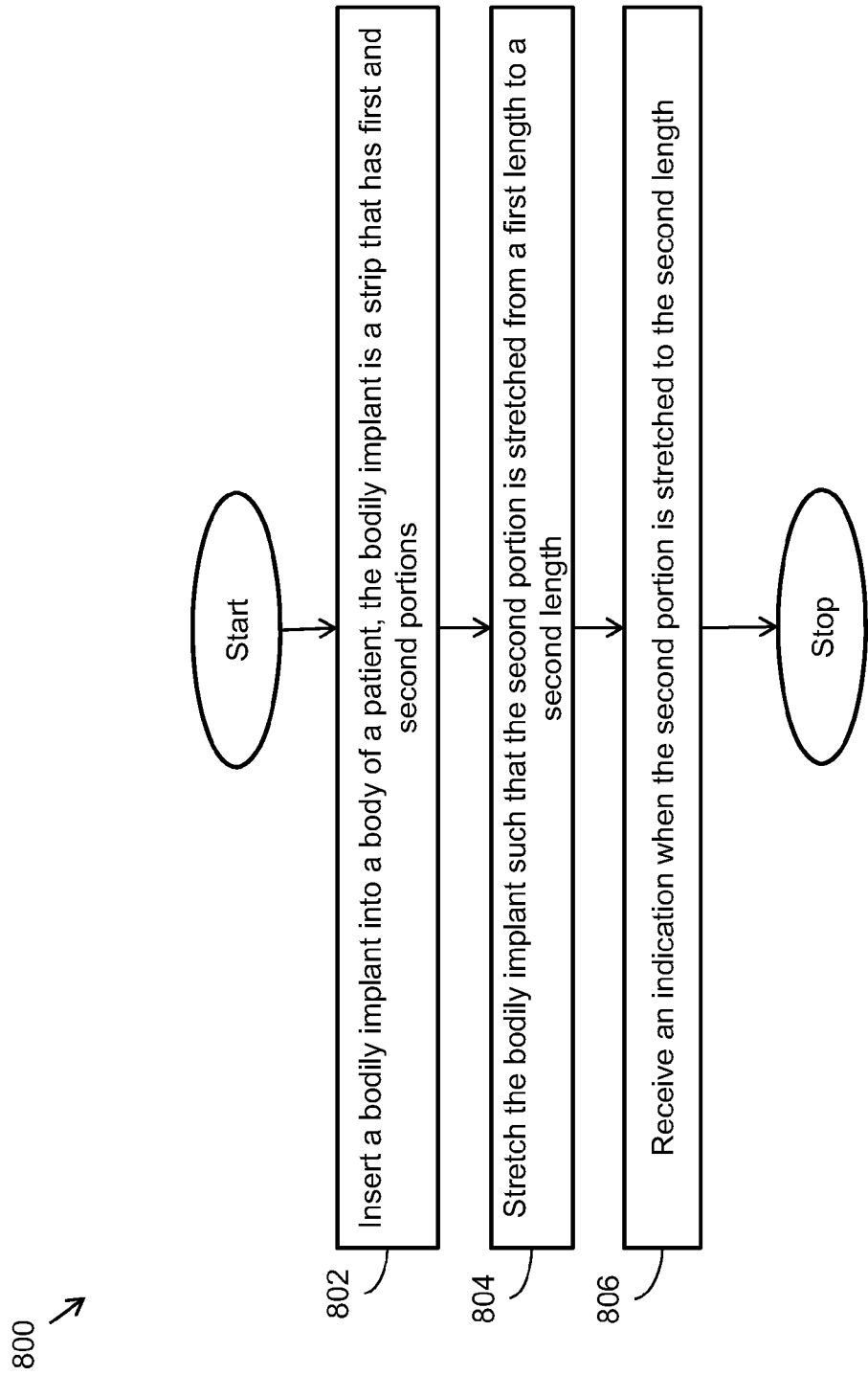
FIG. 8 is a flowchart illustrating a method of implantation of a bodily implant with the patient's body, in accordance with an embodiment of the invention.

FIG. 8 is a flowchart illustrating a method 800 of implantation of a bodily implant with the patient's body, in accordance with an embodiment of the invention. The bodily implant may be any of the bodily implants 100, 200, and 300. At step 802 of the method 800, the operator inserts the bodily implant in a non-stretched configuration into the patient's body. The bodily implant may include a strip (such as 102, 202, or 302) that has a first portion (such as 108, 208, or 308) and a second portion (110, 210a, 210b, 310a, or 310b). In embodiments for the treatment of urinary incontinence, an incision is made in an anterior vaginal wall of the patient and dissected bilaterally to an interior portion of a pelvis of the patient. In various embodiments, two anchors having same shape and size may be configured to be attached to the opposite ends of the bodily implant so as to position the two ends of the bodily implant in place within the body of the patient. In accordance with some embodiments, the anchors may be configured to help retain the bodily implant in place within the patient's body. In accordance with various embodiments, the position of the anchors inside the patient's body is fixed once the anchors are placed inside the patient's body. The operator may use an insertion device (described later in conjunction with FIGS. 9A and 9B) to deliver the support system, including the bodily implant and the anchors, through the vaginal incision and upward into a desired anchoring location around a urethra of the patient.

At step 804, the operator stretches the bodily implant (or the strip) that is disposed between the anchors such that the second portion is stretched from a first length to a second length. The operator may stretch the bodily implant with the second tensile force such that only the second portion of the bodily implant reaches or crosses its stretching point without stretching the rest of the bodily implant. The operator may thus adjust the position of the bodily implant inside the patient's body by pulling the second portion of the bodily implant without causing any change in the position of the anchors.

Finally at step 806, the operator may receive an indication when the second portion is stretched to the second length. In some embodiments, the second portion is configured to provide an indication of the stretching of the second portion, i.e., when the second portion is being stretched to the second length. In other embodiments, the second portion may include an upper layer and a lower layer. In this case, the upper layer may be configured to crack or develop micro-fractures when the bodily implant is stretched to the second length. The cracks or the micro-fractures may result in providing an opening or openings in the bodily implant such that the lower layer, which is immediately below the upper layer, is visible to the operator or physician. In various embodiments, the visibility of the lower layer acts as an indication to the operator that the second portion has been stretched to the second length.

In one embodiment, the operator may stop any further stretching of the bodily implant and hence, this second length is maintained to achieve some slack between the bodily implant and the supported body tissues. In an embodiment for the treatment of urinary incontinence, the bodily implant is designed to provide support to body tissues that form a body organ such as a urethra and a bladder neck. The stretched bodily implant, with the second portion maintained at the second length, may thus be disposed at a first desired location surrounding the urethra so that the contact between the bodily implant and the urethra is neither left too loose nor tight.

Alternatively, in another embodiment, the second portion may be configured to be stretched even further from the second length to a third length in order to achieve a looser contact between the bodily implant and the supported body tissues. In this case, the operator may readjust the position of the bodily implant, with the second portion maintained at this third length, at a second desired location surrounding the urethra of the patient. In an exemplary embodiment, the operator may observe a lighter color of the lower layer as an indication that the second portion has been stretched to the second length. The operator may then further stretch the second portion to the third length at which the operator may observe a consistent dark color of the lower layer. The operator may then stop any further stretching of the bodily implant and hence, the third length of the second portion is maintained. The operator may thus place the bodily implant at the second desired location to achieve an appropriate amount of slack (looser contact as compared to the scenario when the second portion is maintained at the second length) between the bodily implant and the supported body tissues.

Figure 9:
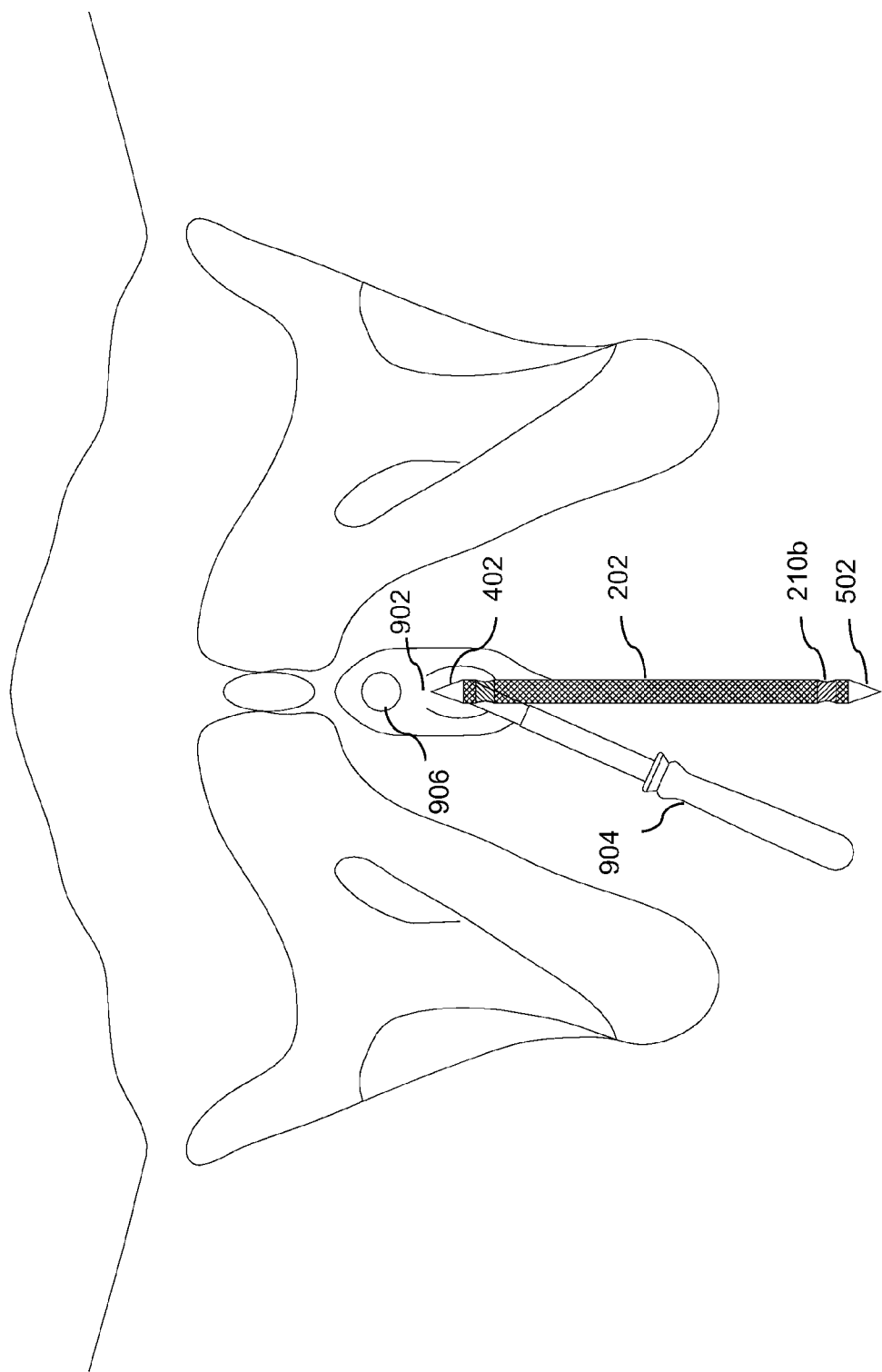
FIG. 9 is an illustrative method of implanting the support system of FIG. 5A within the patient's body, in accordance with an embodiment of the invention.

FIG. 9 is an illustrative method of implanting the support system 500 of FIG. 5A within the patient's body, in accordance with an embodiment of the invention. According to some embodiments, the support system 500 is implanted via an initial transvaginal incision, and thus avoids the need for any abdominal or ishiopubic incision. As shown in FIG. 9, an incision 902 is made in an anterior vaginal wall of the patient and dissected bilaterally to an interior portion of a pelvis of the patient. In this embodiment, the operator may use an insertion device 904 to deliver the support system 500, including the bodily implant 200 and the anchors 402 and 502, inside the patient's body. As shown in FIG. 9, the anchor 402 coupled to the first end 204 of the bodily implant 200 is coupled to, such as by inter-fitting over, a distal end of the insertion device 904. The operator may then pass the insertion device 904 with the anchor 402 through the vaginal incision 902 and upward into a desired anchoring location around a urethra 906 of the patient. The anchoring location may be any suitable abdominal body tissue, such as, but not limited to, a retropubic space between a bladder and an abdomen of the patient. In some embodiments, the anchoring location may be in front of or behind a pubic bone of the patient. As shown in FIG. 9, the anchor 502 is configured to be disposed on the second end 206 of the bodily implant 200. The anchors 402 and 502 may be placed at the desired anchoring locations within the patient's body. The operator may then stretch the bodily implant 200 such that the second portion (210a or 210b) of the bodily implant 200 may be stretched to the second length (i.e., the desired length as described earlier) so that the tension is provided around the urethra 906. The operator may thus adjust the position of the bodily implant 200 inside the patient's body by pulling the second portion (210a or 210b) of the bodily implant 200 without causing any change in the position of the anchors 402 and 502.

As described earlier, the second portion (210a or 210b) may be configured to provide a visual indication when this second portion is being stretched to the second length. In this case, the operator will refrain from any further stretching of the strip 202. In some embodiments, the second portion (210a or 210b) may include an upper layer and a lower layer. In this case, the upper layer may be configured to crack or develop micro-fractures when the bodily implant 200 is stretched to the second length. The cracks or the micro-fractures may result in providing an opening or openings in the bodily implant 200 such that the lower layer, which is immediately below the upper layer, is visible to the operator. In various embodiments, the visibility of the lower layer acts as the indication to the operator that the second portion has been stretched to the desired second length. The operator may then withdraw the insertion device 904 from the patient's body.

FIG. 10 is an illustrative method of positioning the support system 500 of FIG. 5A within the patient's body, in accordance with an embodiment of the invention. This embodiment discloses a stretched configuration of the support system 500 in which the second portion (210a or 210b) of the bodily implant 200 is being stretched to and maintained at the second length. In this case, the procedure of implantation and positioning of the support system 500 is the same as that explained above in conjunction with FIG. 9, except that in FIG. 10 the procedure is performed on the contra-lateral side of the patient's body. As shown in FIG. 10, the anchors 402 and 502 are disposed at the desired locations and then the second portion (210a or 210b) of the bodily implant 200 is stretched to the second length (i.e., the desired length as described earlier) so that the tension is provided around the urethra 906.

FIGS. 9 and 10 are described with respect to the support system 500 of FIG. 5A; however, the support systems of FIGS. 5B, 6A, and 6B may be employed in a similar manner.

The present invention has been described in conjunction with a bodily implant (such as 100, 200, or 300). However, various other types of bodily implants (including conventional devices), slings, support members, suture bundles, pull rods, sleeves, other bolstering materials, and the like may be equally used to be delivered into the patient's body with the use of the teachings of the invention.

The present invention has been described in terms of the treatment of human urinary incontinence. The present invention may find applications in the treatment of several other problems associated with human body such as fecal incontinence, vaginal prolapse, anal prolapse, breast surgery, and the like.

In some embodiments, a bodily implant includes a strip having a first portion and a second portion. The strip is configured to be stretched such that the second portion is stretched from a first length to a second length. The second portion of the strip is configured to maintain the second length. The strip is configured to be disposed proximate to body tissues of a patient to support the body tissues.

In some embodiments, the strip includes a mesh. In some embodiments, the mesh is made of a polymer material. In some embodiments, the polymer material is at least one of polyolefin and silicone rubber.

In some embodiments, the bodily implant includes a first anchor and a second anchor disposed at opposite ends of the strip. The first and second anchors are configured to help retain the strip in place within the patient. In some embodiments, the second portion is configured to provide an indication when the second portion is being stretched to the second length.

In some embodiments, the indication includes a visual indication.

In some embodiments, a bodily implant includes a mesh having a first portion and a second portion. The mesh is configured to be stretched such that the second portion is stretched from a first length to a second length. The second portion of the mesh is configured to maintain the second length. The strip being configured to be disposed proximate to body tissues of a patient to support the body tissues.

In some embodiments, the mesh is made of a polymer material. In some embodiments, the polymer material is at least one of polyolefin and silicone rubber.

In some embodiments, the bodily implant includes a first anchor and a second anchor disposed at opposite ends of the mesh. The first and second anchors are configured to help retain the mesh in place within the patient. In some embodiments, the second portion is configured to provide an indication when the second portion is being stretched to the second length. In some embodiments, the indication includes a visual indication.

In some embodiments, a bodily implant includes a strip having a first portion and a second portion. The strip is configured to be stretched such that the second portion is stretched from a first length to a second length. The second portion of the strip is configured to maintain the second length; and the strip being configured to be disposed proximate to body tissues of a patient to support the body tissues. The second portion includes an upper layer and a lower layer. The upper layer is configured to crack and the lower layer is configured to provide a visual indication when the second portion is stretched to the second length.

In some embodiments, the strip includes a mesh. In some embodiments, the mesh is made of a polymer material. In some embodiments, the polymer material is at least one of polyolefin and silicone rubber.

In some embodiments, the bodily implant includes a first anchor and a second anchor disposed at opposite ends of the strip. The first and second anchors are configured to help retain the strip in place within the patient. In some embodiments, a color of the lower layer of the second portion is visible when the cracks are created in the upper layer. The color of the lower layer acts as the indication that the second portion is being stretched to the second length. In some embodiments, the second portion, includes a middle layer that is disposed between the upper layer and the lower layer.

In some embodiments, a support system includes a strip, a first anchor, and a second anchor. The strip has a first portion and a second portion. The strip is configured to be stretched such that the second portion is stretched from a first length to a second length. The second portion of the strip is configured to maintain the second length. The strip is configured to be disposed proximate to body tissues of a patient to support the body tissues. The first anchor and the second anchor are disposed at opposite ends of the strip. The first and second anchors are configured to help retain the strip in place within the patient.

In some embodiments, the strip includes a mesh. In some embodiments, the mesh is made of a polymer material. In some embodiments, the polymer material is at least one of polyolefin and silicone rubber. In some embodiments, the second portion is configured to provide an indication when the second portion is being stretched to the second length. In some embodiments, the indication includes a visual indication.

In some embodiments, a method for implantation of a bodily implant includes inserting the bodily implant into a body of a patient, the bodily implant including a strip that has a first portion and a second portion; and stretching the bodily implant such that the second portion is stretched from a first length to a second length such that the second portion maintains the second length.

In some embodiments, the strip includes a mesh.

In some embodiments, the method includes disposing a first anchor and a second anchor at opposite ends of the strip, the first and second anchors are configured to help retain the bodily implant in place within the patient.

In some embodiments, the stretching the bodily implant includes creating cracks in an upper layer of the second portion.

In some embodiments, the method includes receiving an indication when the second portion is being stretched to the second length. The indication includes a visual indication of a lower layer of the second portion when the cracks are created in the upper layer.

In some embodiments, a method for implantation of a bodily implant includes inserting the bodily implant into a body of a patient, the bodily implant including a strip that has a first portion and a second portion; stretching the bodily implant such that the second portion is stretched from a first length to a second length; and receiving an indication when the second portion is being stretched to the second length. In some embodiments, the strip includes a mesh.

In some embodiments, the method includes disposing a first anchor and a second anchor at opposite ends of the strip, the first and second anchors are configured to help retain the bodily implant in place within the patient. In some embodiments, the stretching the bodily implant comprises creating cracks in an upper layer of the second portion. In some embodiments, the indication includes a visual indication of a lower layer of the second portion when the cracks are created in the upper layer.

In some embodiments, a method for implantation of a bodily implant includes inserting the bodily implant into a body of a patient, the bodily implant including a strip that has a first portion and a second portion; stretching the bodily implant such that the second portion is stretched from a first length to a second length such that the second portion maintains the second length; and readjusting the bodily implant within the body of the patient such that the second portion is stretched from the second length to a third length such that the second portion maintains the third length.

In some embodiments, a method for implantation of a bodily implant includes inserting the bodily implant into a body of a patient, the bodily implant including a strip that has a first portion and a second portion; stretching the bodily implant such that the second portion is stretched from a first length to a second length; receiving an indication when the second portion is being stretched to the second length; readjusting the bodily implant within the body of the patient such that the second portion is stretched from the second length to a third length; and receiving an indication when the second portion is being stretched to the third length.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A bodily implant comprising:
a strip having a first portion and a second portion, the second portion being formed of a material having a different property than the first portion, the material of the second portion being configured to be stretched such that the second portion is lengthened from a first length to a second length, the material of the second portion of the strip being configured to maintain the second length, and
the strip being configured to be disposed proximate to body tissues of a patient to support the body tissues,
wherein the second portion includes a first layer of material and a second layer of material, the first layer of material and the second layer of material having substantially the same length, the first layer of material being configured to develop micro-fractures when the second portion is stretched to the second length such that a portion of the second layer of material is exposed through the micro-fractures, the first layer of material being constructed from a different material than the second layer of material,
wherein the micro-fractures include openings through a thickness of the first layer of material when the second portion is stretched to the second length, the first layer of material being configured to develop additional openings when the second portion is stretched to a third length, the third length being greater than the second length.

2. The bodily implant of claim 1, wherein the strip includes a mesh.

3. The bodily implant of claim 2, wherein the mesh is made of a polymer material, the polymer material including at least one of polyolefin and silicone rubber.

4. The bodily implant of claim 1, further comprising:
a first anchor and a second anchor disposed at opposite ends of the strip, wherein the first and second anchors are configured to help retain the strip in place within the patient.

5. The bodily implant of claim 1, wherein the second portion is biconcave with a first curvature at the first length and a second curvature at the second length, the second curvature being less than the first curvature.

6. The bodily implant of claim 1, wherein the second portion is disposed adjacent and in between the first portion and an end portion of the strip.

7. The bodily implant of claim 1, wherein the second portion is disposed at a location apart from ends of the strip.

8. The bodily implant of claim 1, wherein the first layer of material and the second layer of material have the same length.

9. A bodily implant comprising:
a mesh having a first portion and a second portion, the first portion having a first stretching threshold such that the first portion is configured to begin to stretch when a tensile force is applied to the mesh that exceeds the first stretching threshold, the second portion having a second stretching threshold such that the second portion is configured to begin to stretch when a tensile force is applied to the mesh that exceeds the second stretching threshold, the second stretching threshold being lower than the first stretching threshold, the second portion being configured to be stretched from a first length to a second length without the first portion being stretched, the second portion of the mesh being configured to maintain the second length,
the mesh being configured to be disposed proximate to body tissues of a patient to support the body tissues,
wherein the second portion of the mesh includes a top layer of material and a bottom layer of material, the top layer of material and the bottom layer of material extending parallel to each other, the top layer of material and the bottom layer of material having the same length, the top layer of material being configured to develop a plurality of micro-fractures when the second portion is stretched to the second length such that a portion of the bottom layer of material is uncovered by the plurality of micro-fractures, the top layer of material being constructed from a different material than the bottom layer of material,
wherein the second portion has a different mesh pattern than the first portion.

10. The bodily implant of claim 9, wherein the second portion includes a concave portion on a first side of the second portion and a concave portion on a second side of the second portion.

11. The bodily implant of claim 9, wherein the second portion includes a polymer material, the polymer material being one of polyolefin and silicone rubber.

12. The bodily implant of claim 9, further comprising:
a first anchor and a second anchor disposed at opposite ends of the mesh, wherein the first and second anchors are configured to help retain the mesh in place within the patient.

13. The bodily implant of claim 9, wherein the bottom layer of material of the second portion includes a visual indicator that is exposed through the plurality of micro-fractures when the second portion is being stretched to the second length.

14. The bodily implant of claim 9, wherein the bottom layer of material is a different color than the top layer of material.

15. A method for implantation of a bodily implant, the method comprising:
inserting the bodily implant into a body of a patient, the bodily implant including a strip that has a first mesh portion and a second mesh portion, the second mesh portion being formed of a material having a different property than the first mesh portion, the second mesh portion including a first layer of material and a second layer of material, the first layer of material and the second layer of material extending parallel to each other, the first layer of material and the second layer of material having the same length;
stretching the bodily implant such that the material of the second mesh portion is stretched from a first length to a second length and the second mesh portion maintains the second length, the first layer of material developing micro-fractures when the second mesh portion is stretched to the second length such that a portion of the second layer of material is exposed through the micro-fractures, the micro-fractures including openings through a thickness of the first layer of material when the second mesh portion is stretched to the second length; and stretching the bodily implant such that the material of the second mesh portion is stretched to a third length, the first layer of material developing additional openings when the second mesh portion is stretched to the third length, the third length being greater than the second length.

16. The method of claim 15, wherein the first and second mesh portions are synthetic.

17. The method of claim 15, further comprising:

disposing a first anchor and a second anchor at opposite ends of the strip, wherein the first and second anchors are configured to help retain the bodily implant in place within the patient.

18. The method of claim 15, wherein, when the second mesh portion is stretched to the second length, the first layer of material creates the micro-fractures while keeping the first layer of material substantially intact.

19. The method of claim 15, wherein the first mesh portion has a first stretching threshold such that the material of the first mesh portion begins to stretch when a first tensile force is applied to the bodily implant that exceeds the first stretching threshold, the second mesh portion having a second stretching threshold such that the material of the second mesh portion begins to stretch when a second tensile force is applied to the bodily implant that exceeds the second stretching threshold, the second stretching threshold being lower than the first stretching threshold, wherein the stretching includes applying the second tensile force to the bodily implant such that the material of the second mesh portion is stretched from the first length to the second length without stretching the first mesh portion.

20. The method of claim 15, wherein the second mesh portion is disposed adjacent and in between the first mesh portion and an end portion of the strip.

* * * * *